(12) United States Patent
Shirtliff et al.

(10) Patent No.: US 8,318,180 B2
(45) Date of Patent: Nov. 27, 2012

(54) **PROTECTIVE VACCINE AGAINST *STAPHYLOCOCCUS AUREUS* BIOFILMS COMPRISING CELL WALL-ASSOCIATED IMMUNOGENS**

(75) Inventors: Mark E. Shirtliff, Ellicott City, MD (US); Graeme O'May, Cockeysville, MD (US); Jeff Leid, Flagstaff, AZ (US)

(73) Assignees: University of Maryland, Baltimore, Baltimore, MD (US); Northern Arizona University, Flagstaff, AZ (US)

( * ) Notice: Subject to any disclaimer, the term of this patent is extended or adjusted under 35 U.S.C. 154(b) by 0 days.

(21) Appl. No.: 13/121,511

(22) PCT Filed: Sep. 23, 2009

(86) PCT No.: PCT/US2009/058114
§ 371 (c)(1),
(2), (4) Date: Mar. 29, 2011

(87) PCT Pub. No.: WO2010/039563
PCT Pub. Date: Apr. 8, 2010

(65) Prior Publication Data
US 2011/0177111 A1    Jul. 21, 2011

Related U.S. Application Data

(60) Provisional application No. 61/101,317, filed on Sep. 30, 2008.

(51) Int. Cl.
*A61K 39/085* (2006.01)
(52) U.S. Cl. ............... 424/237.1; 424/185.1; 424/190.1; 424/193.1; 424/203.1; 530/350
(58) Field of Classification Search .................. None
See application file for complete search history.

(56) References Cited

U.S. PATENT DOCUMENTS
2007/0020746 A1   1/2007   Kunsch et al.
2008/0095777 A1   4/2008   Castado et al.

FOREIGN PATENT DOCUMENTS
WO   WO02059148 A2 *   8/2002
WO   WO02094868 A2 *  11/2002

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999.*
Chothia et al (The EMBO Journal, 1986, 5/4:823-26).*
Gill et al (J.Bacteriol. 2003. 187: 2426-2438).*
Brady et al. ASM 108th General Meeting. Boston, Mass. Session 132D, Abstract D-073. Jun. 3, 2008.*
Brady RA, et al., Immunoglobulins to surface-associated biofilm immunogens provide a novel means of visualization of methicillin-resistant *Staphylococcus aureus* biofilms, Appl Environ Microbiol. Oct. 2007, 73(20): 6612-6619, 2007.
Holden MT, et al., Complete genomes of two clinical *Staphylococcus aureus* strains: evidence for the rapid evolution of virulence and drug resistance, Proc Natl Acad Sci USA, 2004, 101(26): 9786-9791.
Weichhart T, et al., Functional selection of vaccine candidate peptides from *Staphylococcus aureus* whole-genome expression libraries in vitro, Infect Immun. 2003, 71(8): 4633-4641.
International Search Report, PCT/US09/58114, dated May 7, 2010.

* cited by examiner

*Primary Examiner* — Jennifer Graser
(74) *Attorney, Agent, or Firm* — Roylance, Abrams, Berdo & Goodman, L.L.P.

(57) ABSTRACT

Vaccine formulations effective against *Staphylococcus aureus*, including methicillin-resistant *Staphylococcus aureus* (MRSA) are disclosed, as well as methods of using the vaccine formulations in the treatment, prevention and prophylaxis of *Staphylococcus aureus* infections in a subject.

5 Claims, 4 Drawing Sheets

PROTECTIVE VACCINE AGAINST *STAPHYLOCOCCUS AUREUS* BIOFILMS COMPRISING CELL WALL-ASSOCIATED IMMUNOGENS

STATEMENT OF GOVERNMENTAL INTEREST

This invention was made with government support under Grant Number AI069568 awarded by the National Institutes of Health. The government has certain rights in the invention.

BACKGROUND OF THE INVENTION

1. Field of the Invention

The present invention relates to vaccines effective against methicillin-resistant *Staphylococcus aureus* (MRSA) and methicillin-sensitive *Staphylococcus aureus* (MSSA), and to methods of using the vaccines in the treatment, prevention and prophylaxis of MRSA and MSSA in subjects.

2. Related Art

While once only a hospital acquired pathogen, methicillin-resistant *Staphylococcus aureus* (MRSA) infection has spread to the community and is now reaching epidemic proportions. A recent study has found that nearly 19,000 people per year die from MRSA infections in the United States, a death toll higher than that of AIDS (1). In addition, up to 20% of patients who undergo surgery acquire at least one nosocomial infection (2), which is estimated to add $5-10 billion in costs to the US healthcare system (3, 4). *S. aureus* is one of the most common etiologic agents of these infections (5, 6). These numbers of deaths, as well as the associated healthcare costs, do not even take into account the morbidity and mortality caused by methicillin sensitive *S. aureus* (MSSA) strains that still cause the majority of staphylococcal infections. Therefore, the generation of a vaccine that is protective against *S. aureus* would have the potential to significantly reduce the morbidity and mortality associated with these infections. One of the major ways that *S. aureus* is able to persist is through growth as a biofilm, which is recalcitrant to clearance by antimicrobials, further limiting the efficacy of presently-available antimicrobial agents. With fewer appropriate means of treating the illnesses caused by this bacterium, prevention of disease is essential.

There have been several approaches to designing an effective *S. aureus* vaccine. Whole live or killed *S. aureus* vaccines have proved to be largely ineffective in animal models (7, 8). Thus, research has focused on using purified forms of either polysaccharide or protein from the bacterial surface. Much research has centered on the capsular polysaccharide types 5 and 8 (9). One such vaccine, StaphVAX™ demonstrated protective efficacy in animal models of infection; IgG produced as a result of vaccination showed high levels of opsonophagocytosis in vitro (10) and in a Phase III clinical trial. However, protection waned with time and by one year post-vaccination, it was less than 30% (11). Active or passive immunization with polysaccharide intracellular adhesin (PIA), the principal exopolysaccharide component of *S. aureus* and *S. epidermidis* biofilms, has been shown to be protective against *S. aureus* infection in a kidney infection model (12). However, recent research has illustrated that only one component of PIA is immunogenic and responses to this antigen are variable (13). Deacetylation of PNAG, as well as conjugation to diphtheria toxin as a carrier protein, does help increase protection levels (14). However, not all clinical isolates of either *S. aureus* or *S. epidermidis* produce PIA (15-18), making the relevance of such a vaccine questionable.

Protein-based vaccines have focused mainly on the 'microbial surface components recognizing adhesive matrix molecules' (MSCRAMM) subset of cell wall-associated proteins. Individual component vaccines consisting of clumping factor A (ClfA), ClfB, iron-regulated surface determinant B (IsdB), and fibronectin-binding protein (FnBBP) have all been tested. Recombinant ClfA was shown to be only partially protective when used in an animal model of septic arthritis (19). ClfA is also being investigated as a DNA vaccine candidate in mice and cattle. However, while injection of plasmid containing clfA increased clearance in a mastitis model, protection was not generated against infection in an intraperitoneal challenge (20). Immunization with rClfB led to lessened colonization of murine nares by *S. aureus* (21). Vaccination with IsdB led to increased survival rates of 20-40% in a murine sepsis model (22). A fusion protein consisting of the binding regions of Cna (collagen binding protein) and FnBP showed some protection in a mouse intraperitoneal model (23).

The vaccines discussed above have several limitations, including incomplete protection and the differential expression of the component proteins amongst *S. aureus* isolates (24, 25). Use of a multi-component vaccine has shown promise in promoting significant protection against *S. aureus* infection. When IsdA and B, as well as SdrD and SdrE, were combined into a single vaccine, complete protection was afforded in a mouse renal abscess model, with bacterial levels being reduced below levels of detection and a lack of clinical signs of disease (26).

Even with the advancements being made in this field, the vast majority of research focuses on protection from acute, planktonic-associated *S. aureus* infection. Also, the studies discussed above all make use of non-biofilm animal models of infection. A number of groups (27-30) have shown that gene expression and protein production between the two states of biofilm and planktonic modes of growth differ greatly. Therefore, the vaccine candidates that prevent infection in acute, planktonic-associated models (for example, sepsis, intraperitoneal infection, and renal abscess models) may not be effective against biofilm infections like osteomyelitis, endocarditis, or prosthetic implant infections.

Previous work identified several cell wall-associated proteins that are immunogenic during *S. aureus* biofilm infection and whose genes are up-regulated during biofilm growth (27). Vaccination with a recombinant form of one of these proteins (autolysin) led to significant decreases in biofilm disease severity and symptoms in the same biofilm infection model but no decrease in bacterial levels. Since vaccination was directed against a biofilm up-regulated antigen, the inability of the host to clear the infection may have been due to the persistence of planktonic populations. Therefore, the administration of antimicrobial agents, while not effective against biofilm communities, may be required for clearance of the remaining planktonic staphylococci. In addition, the tested antigen, as well as other biofilm up-regulated antigens, may not be homogenously produced throughout the biofilm, making it impossible for the host to appropriately respond to the entire infectious microbial community.

Accordingly, novel vaccines that are effective in the prevention and treatment of MRSA and MSSA, along with methods of prevention and treatment that utilize such vaccines, are required.

SUMMARY OF THE INVENTION

*S. aureus* has re-emerged as a major human pathogen and there are presently no vaccines that afford consistent, long-term protection against *S. aureus* infections. While infections, particularly those with MRSA, are often nosocomial in origin, community acquired infections associated with this microbial species have reached epidemic levels. One of the ways in which *S. aureus* is able to persist in the host and remain recalcitrant to clearance by the immune system or antimicrobial agents is through a biofilm mode of growth. Therefore, the need for an effective vaccine and/or treatment modality that could prevent the establishment of biofilm-mediated chronic infections by *S. aureus* is necessary.

The present invention demonstrates protection against biofilm-associated *S. aureus* infection through the use of a multi-component vaccine, alone or in combination with subsequent antimicrobial agent therapy. When administered to New Zealand White rabbits, the combination of biofilm-specific vaccination and antimicrobial agent treatment was able to significantly lessen the radiological and clinical signs of infection, and afforded complete clearance to 87.5% of animals, reducing bacterial loads overall by over 3 logs in the one combination vaccinated and treated animal that was found to have persistent staphylococci at the end of the study.

The vaccine of the present invention holds significant promise for those with identified risk factors for *S. aureus* biofilm infection. Even in patients that acquire a *S. aureus* infection, an anti-biofilm vaccine could allow these previously untreatable infections to be cured via antimicrobial agents alone, whereas previously the only reliable therapy was surgical intervention. The present invention thus provides new means to limit and eradiate *S. aureus* biofilm infections that could help to prevent the onset of chronic disease, saving patients from significant morbidity and mortality.

The present invention is thus directed to a number of embodiments of vaccines.

In one embodiment the present invention is directed to a vaccine formulation comprising at least a portion of two different polypeptides of a strain of *Staphylococcus aureus* (a first and a second polypeptide of a strain of *Staphylococcus aureus*) and a pharmaceutically acceptable carrier or diluent. The strain of *Staphylococcus aureus* may be a methicillin-resistant or a methicillin-sensitive strain of *Staphylococcus aureus*. In a preferred embodiment the first and second polypeptides are individually selected from the group consisting of *Staphylococcus aureus* glucosaminidase as set forth in SEQ ID NO:1, *Staphylococcus aureus* polypeptide SA0688 as set forth in SEQ ID NO:2, *Staphylococcus aureus* polypeptide SA0037 as set forth in SEQ ID NO:3, and *Staphylococcus aureus* polypeptide SA0486 as set forth in SEQ ID NO:4. In a further preferred embodiment, the portions of the two *Staphylococcus aureus* polypeptides comprising the vaccine formulation each individually encompass at least about 20 contiguous amino acids of the full length polypeptide.

In a second embodiment the present invention is directed to a vaccine formulation comprising at least a portion of three different polypeptides of a strain of *Staphylococcus aureus* (a first, a second, and a third polypeptide of a strain of *Staphylococcus aureus*) and a pharmaceutically acceptable carrier or diluent. The strain of *Staphylococcus aureus* may be a methicillin-resistant or a methicillin-sensitive strain of *Staphylococcus aureus*. In a preferred embodiment the first, second and third polypeptides are individually selected from the group consisting of *Staphylococcus aureus* glucosaminidase as set forth in SEQ ID NO:1, *Staphylococcus aureus* polypeptide SA0688 as set forth in SEQ ID NO:2, *Staphylococcus aureus* polypeptide SA0037 as set forth in SEQ ID NO:3, and *Staphylococcus aureus* polypeptide SA0486 as set forth in SEQ ID NO:4. In a further preferred embodiment, the portions of the three *Staphylococcus aureus* polypeptides comprising the vaccine formulation each individually encompass at least about 20 contiguous amino acids of the full length polypeptide.

In a third embodiment the present invention is directed to a vaccine formulation comprising at least a portion of four different polypeptides of a strain of *Staphylococcus aureus* (a first, a second, a third and a fourth polypeptide of a strain of *Staphylococcus aureus*) and a pharmaceutically acceptable carrier or diluent. The strain of *Staphylococcus aureus* may be a methicillin-resistant or a methicillin-sensitive strain of *Staphylococcus aureus*. In a preferred embodiment the first, second, third and fourth polypeptides are *Staphylococcus aureus* glucosaminidase as set forth in SEQ ID NO:1, *Staphylococcus aureus* polypeptide SA0688 as set forth in SEQ ID NO:2, *Staphylococcus aureus* polypeptide SA0037 as set forth in SEQ ID NO:3, and *Staphylococcus aureus* polypeptide SA0486 as set forth in SEQ ID NO:4. In a further preferred embodiment, the portions of the four *Staphylococcus aureus* polypeptides comprising the vaccine formulation each individually encompass at least about 20 contiguous amino acids of the full length polypeptide.

In a fourth embodiment the present invention is directed to a vaccine formulation comprising four *Staphylococcus aureus* polypeptides and a pharmaceutically acceptable carrier or diluent. In a preferred embodiment the *Staphylococcus aureus* polypeptides are (i) *Staphylococcus aureus* glucosaminidase as set forth in SEQ ID NO:1, (ii) *Staphylococcus aureus* polypeptide SA0688 as set forth in SEQ ID NO:2, (iii) *Staphylococcus aureus* polypeptide SA0037 as set forth in SEQ ID NO:3, and *Staphylococcus aureus* polypeptide SA0486 as set forth in SEQ ID NO:4.

The present invention is also directed to a number of embodiments of methods of using the vaccines of the invention.

In one embodiment the present invention is directed to methods of generating an immune response in a subject comprising administering an immunologically effective amount of a vaccine formulation of the present invention to a subject, thereby generating an immune response in a subject.

In a second embodiment the present invention is directed to methods of generating a protective immune response in a subject comprising administering an immunologically effective amount of a vaccine formulation of the present invention to a subject, thereby generating a protective immune response in a subject.

In a third embodiment the present invention is directed to methods of inhibiting a *Staphylococcus aureus* infection in a subject, comprising administering a therapeutically effective amount of a vaccine formulation of the present invention to a subject at risk of developing a *Staphylococcus aureus* infection, thereby inhibiting a *Staphylococcus aureus* infection in a subject.

In a fourth embodiment the present invention is directed to methods for providing prophylaxis of a *Staphylococcus aureus* infection in a subject, comprising administering a therapeutically effective amount of a vaccine formulation the present invention to a subject having a *Staphylococcus aureus* infection, thereby for providing prophylaxis of a *Staphylococcus aureus* infection in a subject.

In a related embodiment, the method for providing prophylaxis of a *Staphylococcus aureus* infection further comprises administering an antimicrobial agent to the subject having a *Staphylococcus aureus* infection, wherein the antimicrobial agent is administered prior to, concurrent with or after the vaccine formulation. In these embodiments the antimicrobial agent may be selected from the group that includes, but is not limited to, an Aminoglycoside, such as Amikacin, Gentamicin, Kanamycin, Neomycin, Netilmicin, Streptomycin, Tobramycin or Paromomycin; a Carbacephem, such as Loracarbef; a Carbapenem, such as Ertapenem, Doripenem, Imipenem/Cilastatin or Meropenem; a Cephalosporin, such as Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime or Ceftobiprole; a Glycopeptide, such as Teicoplanin or vancomycin; a Macrolide, such as Azithromycin, Clarithromycin, Dirithromycin, Erythromycin, Erythroped, Roxithromycin, Troleandomycin, Telithromycin or Spectinomycin; a Monobactam, such as Aztreonam; a Penicillin, such as Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin or Ticarcillin; a Polypeptide, such as Bacitracin, Colistin or Polymyxin B; a Quinolone, such as Ciprofloxacin, Enoxacin, Gatifloxacin, Levofloxacin, Lomefloxacin, Moxifloxacin, Norfloxacin, Ofloxacin or Trovafloxacin; a Sulfonamide, such as Mafenide, Prontosil (archaic), Sulfacetamide, Sulfamethizole, Sulfanilimide (archaic), Sulfasalazine, Sulfisoxazole, Trimethoprim or Trimethoprim-Sulfamethoxazole (Cotrimoxazole) (TMP-SMX); a Tetracycline, such as Demeclocycline, Doxycycline, Minocycline, Oxytetracycline or Tetracycline; as well as Chloramphenicol, Clindamycin, Lincomycin, Fusidic acid, Furazolidone, Linezolid, Metronidazole, Mupirocin, Nitrofurantoin, Macrobid, Platensimycin, Quinupristin/Dalfopristin, Rifampin or Rifampicin.

In each of these embodiments the *Staphylococcus aureus* infection may be any *Staphylococcus aureus* of a subject, including, for example, a *Staphylococcus aureus* biofilm infection, a *Staphylococcus aureus* osteomyelitis infection, a biofilm-associated *Staphylococcus aureus* osteomyelitis infection, a *Staphylococcus aureus* indwelling medical device infection, a *Staphylococcus aureus* endocarditis infection, a *Staphylococcus aureus* diabetic wound or ulcer infection, a *Staphylococcus aureus* chronic rhinosinusitis infection, a *Staphylococcus aureus* ventilator associated pneumonia infection, a *Staphylococcus aureus* intravenous catheter associated infection, a *Staphylococcus aureus* skin infection, a *Staphylococcus aureus* nectrotizing fasciitis, a *Staphylococcus aureus* keratitis, a *Staphylococcus aureus* endophthlamitis, a *Staphylococcus aureus* pyopneumothorax, a *Staphylococcus aureus* empyema, and a *Staphylococcus aureus* septicemia.

In a fifth embodiment the present invention is directed to methods of treating a *Staphylococcus aureus* infection in a subject, comprising administering a therapeutically effective amount of a vaccine formulation of the present invention to a subject having a *Staphylococcus aureus* infection, thereby treating a *Staphylococcus aureus* infection in a subject.

In a related embodiment, the method of treatment further comprises administering an antimicrobial agent to the subject having a *Staphylococcus aureus* infection, wherein the antimicrobial agent is administered prior to, concurrent with or after the vaccine formulation. In these embodiments the antimicrobial agent may be selected from the group that includes, but is not limited to, an Aminoglycoside, such as Amikacin, Gentamicin, Kanamycin, Neomycin, Netilmicin, Streptomycin, Tobramycin or Paromomycin; a Carbacephem, such as Loracarbef; a Carbapenem, such as Ertapenem, Doripenem, Imipenem/Cilastatin or Meropenem; a Cephalosporin, such as Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime or Ceftobiprole; a Glycopeptide, such as Teicoplanin or vancomycin; a Macrolide, such as Azithromycin, Clarithromycin, Dirithromycin, Erythromycin, Erythroped, Roxithromycin, Troleandomycin, Telithromycin or Spectinomycin; a Monobactam, such as Aztreonam; a Penicillin, such as Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin or Ticarcillin; a Polypeptide, such as Bacitracin, Colistin or Polymyxin B; a Quinolone, such as Ciprofloxacin, Enoxacin, Gatifloxacin, Levofloxacin, Lomefloxacin, Moxifloxacin, Norfloxacin, Ofloxacin or Trovafloxacin; a Sulfonamide, such as Mafenide, Prontosil (archaic), Sulfacetamide, Sulfamethizole, Sulfanilimide (archaic), Sulfasalazine, Sulfisoxazole, Trimethoprim or Trimethoprim-Sulfamethoxazole (Cotrimoxazole) (TMP-SMX); a Tetracycline, such as Demeclocycline, Doxycycline, Minocycline, Oxytetracycline or Tetracycline; as well as Chloramphenicol, Clindamycin, Lincomycin, Fusidic acid, Furazolidone, Linezolid, Metronidazole, Mupirocin, Nitrofurantoin, Macrobid, Platensimycin, Quinupristin/Dalfopristin, Rifampin or Rifampicin.

In each of these embodiments the *Staphylococcus aureus* infection may be any *Staphylococcus aureus* of a subject, including, for example, a *Staphylococcus aureus* biofilm infection, a *Staphylococcus aureus* osteomyelitis infection, a biofilm-associated *Staphylococcus aureus* osteomyelitis infection, a *Staphylococcus aureus* indwelling medical device infection, a *Staphylococcus aureus* endocarditis infection, a *Staphylococcus aureus* diabetic wound or ulcer infection, a *Staphylococcus aureus* chronic rhinosinusitis infection, a *Staphylococcus aureus* ventilator associated pneumonia infection, a *Staphylococcus aureus* intravenous catheter associated infection, a *Staphylococcus aureus* skin infection, a *Staphylococcus aureus* nectrotizing fasciitis, a *Staphylococcus aureus* keratitis, a *Staphylococcus aureus* endophthlamitis, a *Staphylococcus aureus* pyopneumothorax, a *Staphylococcus aureus* empyema, and a *Staphylococcus aureus* septicemia.

DETAILED DESCRIPTION

Figure 1:
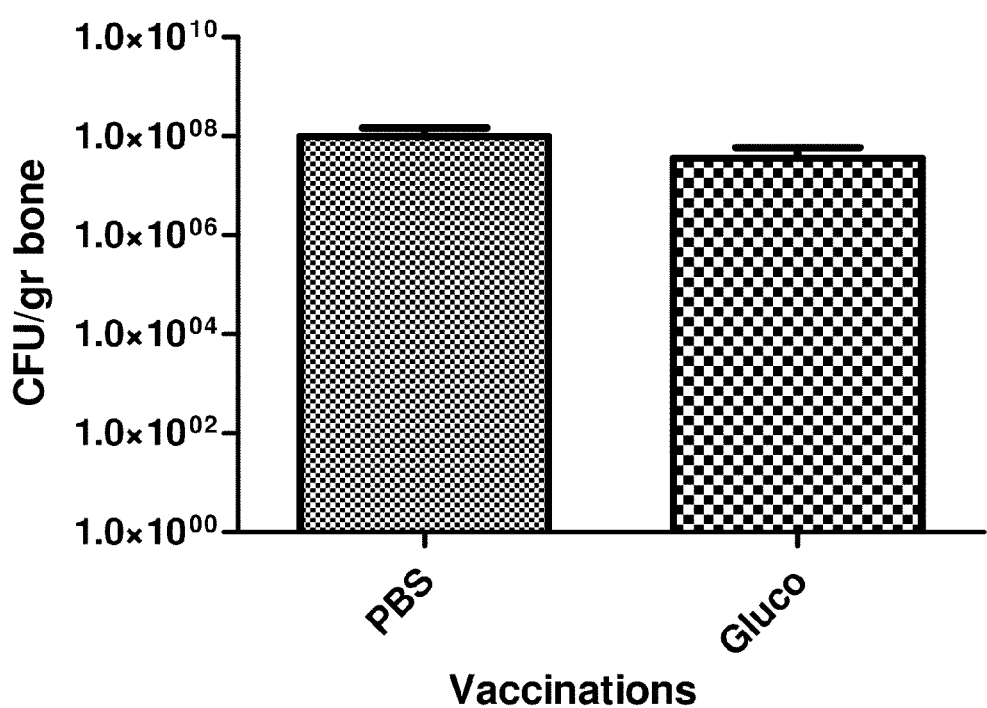
FIG. 1: Glucosaminidase vaccination does not significantly lower CFU levels in affected tibias. Mean CFU/grams bone for PBS controls: $9.84 \times 10^7$; mean CFU/grams bone for glucosaminidase: $3.6 \times 10^7$.

As discussed above and herein, the present invention relates to vaccine formulations effective against *Staphylococcus aureus*, including methicillin-resistant *Staphylococcus aureus* (MRSA) and methicillin-sensitive *Staphylococcus aureus* (MSSA), and to methods of using the vaccines in the treatment, prevention and prophylaxis of *Staphylococcus aureus* infections in a subject.

The vaccine formulations of the present invention comprise at least a portion of two different polypeptides of a strain of *Staphylococcus aureus* and a pharmaceutically acceptable carrier or diluent. The skilled artisan will understand that the number, type, identity and size of the different *Staphylococcus aureus* polypeptides that can be included in the vaccine formulations of the present invention can vary. Thus, with regard to the number of different peptides or polypeptides included in formulations of the invention, at least a portion of two, three, four, five, six, seven, eight, nine, ten or more different polypeptides of a strain of *Staphylococcus aureus* may be included. Similarly, two, three, four, five, six or more different portions of the same polypeptide of *Staphylococcus aureus* can be used in the formulations, either in combination with each other (i.e., all peptides in the formulation are derived from the same polypeptide) or in combination with other peptides and/or polypeptides *Staphylococcus aureus*. In yet another example a formulation of the present invention can include portions of one or more polypeptides of *Staphylococcus aureus* as well as full length versions of the same or different *Staphylococcus aureus* polypeptides. In a preferred embodiment, the vaccine formulations of the present invention comprise at least one portion of four different polypeptides of *Staphylococcus aureus*. In a further preferred embodiment, the vaccine formulations of the present invention comprise at least four different full-length polypeptides of *Staphylococcus aureus*.

The identity of the peptides and polypeptides included in the vaccine formulations of the present invention is not particularly limited but each is a peptide or polypeptide from a strain of *Staphylococcus aureus*. However, because the primary purpose of the vaccine formulations is to prime and activate the immune system of the subject receiving the vaccine formulation, the use of peptides and polypeptides exposed on the surface of the bacteria is particularly preferred. For example, the polypeptides may be cell wall and cell wall-associated polypeptides of *Staphylococcus aureus*, or peptide portions thereof. Examples of such polypeptides include the *Staphylococcus aureus* polypeptides glucosaminidase (SEQ ID NO:1), SA0688 (SEQ ID NO:2), SA0037 (SEQ ID NO:3) and SA0486 (SEQ ID NO:4).

As indicated above, the polypeptides used in the formulations of the present invention are from strains of *Staphylococcus aureus*. There is no limitation on the different strains of *Staphylococcus aureus* that might be used. As an example only, polypeptides from medically important strains of *Staphylococcus aureus*, such methicillin-resistant *Staphylococcus aureus* (either community-associated or hospital-acquired strains) and methicillin-sensitive *Staphylococcus aureus*, may be used to constitute the vaccine formulations of the present invention.

When only a portion of a polypeptide is used in a vaccine formulation, the size of the peptide is only limited by its ability to be recognized by the immune system of the subject to which the vaccine is administered. In general, the peptides included in the formulations should be about 4, 5, 6, 7, 8, 9, 10, 11, 12, 13, 14, 15, 16, 17, 18, 19, 20, 21, 22, 23, 24, 25 or more amino acids in length. The preferred size of the peptides is between about 20 amino acids and 3000 amino acids in length, more preferably between about 40 amino acids and 1500 amino acids in length, even more preferably between about 150 amino acids and 1300 amino acids in length.

The vaccine formulations of the present invention also include the use of peptides and polypeptides having at least about 70%, 75%, 80%, 85%, 90%, 91%, 92%, 93%, 94%, 95%, 96%, 97%, 98% or 99% sequence identity to any of the peptides or polypeptides described herein for use in the vaccine formulations of the present invention, including the *Staphylococcus aureus* polypeptides glucosaminidase (SEQ ID NO:1), SA0688 (SEQ ID NO:2), SA0037 (SEQ ID NO:3), SA0486 (SEQ ID NO:4). Sequence identity is determined by aligning the amino acid sequence of two peptides or proteins and calculating the number of amino acid differences over the entire length of the alignment. The skilled artisan will understand that there are a number of commercially available sequence manipulation programs for use in making such calculations, including the website of the National Center for Biotechnology Information.

The peptides and polypeptides used in the vaccine formulations may be obtained through any of the many well-established means known in the art. The skilled artisan will understand that the peptides and polypeptides can posses the native glycosylation of polypeptide as it is produced by the corresponding strain of *Staphylococcus aureus*, or they can lack such glycosylation, or they can have altered glycosylation.

The vaccine formulations of the present invention may comprise different amounts of the particular peptides and polypeptides from which they are prepared. Further, the total amount of protein in the formulations will vary based on the particular use to which the formulations are put (e.g., administration to the subject pre- or post-exposure to *Staphylococcus aureus*), the age and size of the subject, and the general health of the subject, to name only a few factors to be considered. In general, however, the vaccine formulations of the present invention will comprise sufficient *Staphylococcus aureus* protein to induce an immune response in a subject to the components of the vaccine. For example, the vaccines formulations may contain between about 1 to about 1000 ug of total *Staphylococcus aureus* protein per kg of body weight of the subject to which the dose of the vaccine formulation will be administered, more preferably between about 10 to about 200 ug, even more preferably between about 15 to about 100 ug.

The pharmaceutically acceptable carrier, diluent or excipient included in the vaccine formulations will vary based on the identity of the *Staphylococcus aureus* proteins in the formulation, the means used to administer the formulation, the site of administration and the dosing schedule used. Suitable examples of carriers and diluents are well known to those skilled in the art and include water-for-injection, saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, liposheres, vesicles, particles, and liposomes. The terms specifically exclude cell culture medium. Additional carriers include cornstarch, gelatin, lactose, sucrose, microcrystalline cellulose, kaolin, mannitol, dicalcium phosphate, sodium chloride, alginic acid, croscarmellose sodium, and sodium starch glycolate.

Excipients included in a formulation have different purposes depending, for example on the nature of the vaccine formulation and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweetners, perfuming agents, flavouring agents, coloring agents, administration aids, and combinations thereof.

As a specific example, intramuscular preparations can be prepared and administered in a pharmaceutically acceptable diluent such as Water-for-Injection, 0.9% saline, or 5% glucose solution.

In one embodiment of the present invention, the vaccine formulations exist as atomized dispersions for delivery by inhalation. The atomized dispersion of the vaccine formulation typically contains carriers common for atomized or aerosolized dispersions, such as buffered saline and/or other compounds well known to those of skill in the art. The delivery of the vaccine formulations via inhalation has the effect of rapidly dispersing the vaccine formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the vaccines and vaccine formulations may also be administered in a liquid form. The liquid can be for oral dosage, for ophthalmic or nasal dosage as drops, or for use as an enema or douche. When the vaccine formulation is formulated as a liquid, the liquid can be either a solution or a suspension of the vaccine formulation. There are a variety of suitable formulations for the solution or suspension of the vaccine formulation that are well know to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

The vaccine formulations of the present invention may also include an adjuvant. Suitable adjuvants include Freund's Complete and Incomplete Adjuvant, Titermax, Oil in Water Adjuvants, as well as Aluminum compounds where antigens, normally proteins, are physically precipitated with hydrated insoluble salts of aluminum hydroxide or aluminum phosphate. Other adjuvants include liposome-type adjuvants comprising spheres having phospholipid bilayers that form an aqueous compartment containing the vaccine candidate and protecting it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli*. Immunomodulation through the use of anti-IL-17, anti IFN-γ, anti-IL-12, IL-2, IL-10, or IL-4 may also be used to promote a strong Th2 or antibody mediated response to the vaccine formulation.

The present invention is also directed to methods of generating an immune response in a subject to a vaccine formulation of the present invention. In one embodiment, the present invention is directed to methods of generating an immune response in a subject, comprising administering an immunologically effective amount of a vaccine formulation of the present invention to a subject, thereby generating an immune response in a subject. In each of the methods of generating an immune response of the present invention, the immune response is preferably a protective immune response.

An "immunologically effective amount" of a vaccine formulation is one that is sufficient to induce an immune response to vaccine components in the subject to which the vaccine formulation is administered. A "protective immune response" is one that confers on the subject to which the vaccine formulation is administered protective immunity against the strain of *Staphylococcus aureus* from which the proteins of the formulation were obtained. The protective immunity may be partial or complete immunity.

The vaccine formulations of the present invention may also be used in methods of inhibiting a *Staphylococcus aureus* infection in a subject. Such methods comprise administering a therapeutically effective amount of a vaccine formulation of the present invention to a subject at risk of developing a *Staphylococcus aureus* infection, thereby inhibiting a *Staphylococcus aureus* infection in a subject. In a preferred embodiment, the method further comprises administering an antimicrobial agent to the subject at risk of developing a *Staphylococcus aureus* infection in conjunction with the administration of the vaccine formulation.

A "therapeutically effective amount" of a vaccine formulation is one that is sufficient to provide at least some reduction in the symptoms of a *Staphylococcus aureus* infection in a subject to which the vaccine formulation is administered.

As used herein, the terms "inhibit", "inhibiting" and "inhibition" have their ordinary and customary meanings, and include one or more of inhibiting colonization of *Staphylococcus aureus*, inhibiting growth of *Staphylococcus aureus* (all forms, including planktonic and biofilm) and inhibiting propagation of *Staphylococcus aureus*. Such inhibition is an inhibition of about 1% to about 100% versus a subject to which the vaccine formulation of the present invention has not been administered (with or without the additional administration of the antimicrobial agent). Preferably, the inhibition is an inhibition of 100%, 99%, 98%, 97%, 96%, 95%, 90%, 80%, 70%, 60%, 50%, 40%, 30%, 20%, 10%, 5% or 1%. As used herein, the inhibition lasts at least a period of days, weeks, months or years upon completing of the dosing schedule. Preferably the inhibition is for the lifespan of the subject.

The present invention is also directed to methods for providing prophylaxis of a *Staphylococcus aureus* infection in a subject using the vaccine formulations of the present invention. In one embodiment, the present invention is directed to methods for providing prophylaxis of a *Staphylococcus aureus* infection in a subject, comprising administering a therapeutically effective amount of a vaccine formulation of the present invention to a subject having a *Staphylococcus*

*aureus* infection, thereby providing prophylaxis of a *Staphylococcus aureus* infection in a subject. In a preferred embodiment, the method further comprises administering an antimicrobial agent to the subject having a *Staphylococcus aureus* infection in conjunction with the administration of the vaccine formulation.

As used herein, "prophylaxis" includes inhibiting the development of a productive or progressive infection by *Staphylococcus aureus* in a subject, where the prophylaxis lasts at least 1, 5, 10, 15, 20, 25, 30, 35, 40, 45, 50, 55, 60, or more days after administration of a vaccine formulation the present invention (with or without the additional administration of the antimicrobial agent). Inhibition against development of a productive or progressive infection by *Staphylococcus aureus* means that the severity of a *Staphylococcus aureus* infection in a subject is reduced by about 1% to about 100% versus a subject to which a vaccine formulation of the present invention has not been administered (with or without the additional administration of the antimicrobial agent). Preferably, the reduction in severity is a 100%, 99%, 98%, 97%, 96%, 95%, 90%, 80%, 70%, 60%, 50%, 40%, 30%, 20%, 10%, 5% or 1% reduction in severity. The severity of an infection may be based on the amount of *Staphylococcus aureus* present in a subject, the length of time that *Staphylococcus aureus* can be detected in a subject, and/or the severity of a symptom of *Staphylococcus aureus* infection, among other factors.

The present invention is also directed to methods of treating a *Staphylococcus aureus* infection in a subject using the vaccine formulations of the present invention. In one embodiment, the present invention is directed to methods of treating a *Staphylococcus aureus* infection in a subject, comprising administering a therapeutically effective amount of a vaccine formulation of the present invention to a subject having a *Staphylococcus aureus* infection, thereby treating a *Staphylococcus aureus* infection in a subject. In a preferred embodiment, the method further comprises administering an antimicrobial agent to the subject having a *Staphylococcus aureus* infection in conjunction with the administration of the vaccine formulation.

As used herein, the terms "treating" and "treatment" have their ordinary and customary meanings, and include one or more of, ameliorating a symptom of a *Staphylococcus aureus* infection in a subject, blocking or ameliorating a recurrence of a symptom of a *Staphylococcus aureus* infection in a subject, decreasing in severity and/or frequency a symptom of a *Staphylococcus aureus* infection in a subject, as stasis, decreasing, or inhibiting growth of *Staphylococcus aureus* in a subject. Treatment means ameliorating, blocking, reducing, decreasing or inhibiting by about 1% to about 100% versus a subject to which the vaccine formulation of the present invention has not been administered (with or without the additional administration of the antimicrobial agent). Preferably, the ameliorating, blocking, reducing, decreasing or inhibiting is 100%, 99%, 98%, 97%, 96%, 95%, 90%, 80%, 70%, 60%, 50%, 40%, 30%, 20%, 10%, 5% or 1%. The treatment may begin prior to, concurrent with, or after the onset of clinical symptoms of the infection. The results of the treatment may be permanent, such as where the *Staphylococcus aureus* infection is completely cleared from the subject, or may be for a period of days (such as 1, 2, 3, 4, 5, 6 or 7 days), weeks (such as 1, 2, 3 or 4 weeks) or months (such as 1, 2, 3, 4, 5, 6 or more months).

When an antimicrobial agent is included in the methods of the present invention the antimicrobial agent may be administered prior to, concurrent with or after the vaccine formulation is administered to the subject. Where the antimicrobial agent is administered prior to or after the vaccine formulation, the period of time between when the antimicrobial agent and the vaccine formulation are administered may be a period of hours (such as 6, 12, 18 or 24 hours), days (such as 1, 2, 3, 4, 5, 6 or 7 days), weeks (such as 1, 2, 3 or 4 weeks) or months (such as 1, 2, 3, 4, 5, 6 or more months). The antimicrobial agent may be any that is effective in the treatment of a *Staphylococcus aureus* infection and may include, but is not limited to, an Aminoglycoside, such as Amikacin, Gentamicin, Kanamycin, Neomycin, Netilmicin, Streptomycin, Tobramycin or Paromomycin; a Carbacephem, such as Loracarbef; a Carbapenem, such as Ertapenem, Doripenem, Imipenem/Cilastatin or Meropenem; a Cephalosporin, such as Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime or Ceftobiprole; a Glycopeptide, such as Teicoplanin or vancomycin; a Macrolide, such as Azithromycin, Clarithromycin, Dirithromycin, Erythromycin, Erythroped, Roxithromycin, Troleandomycin, Telithromycin or Spectinomycin; a Monobactam, such as Aztreonam; a Penicillin, such as Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin or Ticarcillin; a Polypeptide, such as Bacitracin, Colistin or Polymyxin B; a Quinolone, such as Ciprofloxacin, Enoxacin, Gatifloxacin, Levofloxacin, Lomefloxacin, Moxifloxacin, Norfloxacin, Ofloxacin or Trovafloxacin; a Sulfonamide, such as Mafenide, Prontosil (archaic), Sulfacetamide, Sulfamethizole, Sulfanilimide (archaic), Sulfasalazine, Sulfisoxazole, Trimethoprim or Trimethoprim-Sulfamethoxazole (Cotrimoxazole) (TMP-SMX); a Tetracycline, such as Demeclocycline, Doxycycline, Minocycline, Oxytetracycline or Tetracycline; as well as Chloramphenicol, Clindamycin, Lincomycin, Fusidic acid, Furazolidone, Linezolid, Metronidazole, Mupirocin, Nitrofurantoin, Macrobid, Platensimycin, Quinupristin/Dalfopristin, Rifampin or Rifampicin.

In each of the methods of the present invention the vaccine formulations are administered in a pharmaceutically acceptable form and in substantially non-toxic quantities. The vaccine formulations may be administered to a subject using different dosing schedules, depending on the particular use to which the formulations are put (e.g., administration to the subject pre- or post-exposure to *Staphylococcus aureus*), the age and size of the subject, and the general health of the subject, to name only a few factors to be considered. In general, the vaccine formulations may be administered once, or twice, three times, four times, five times, six times or more, over a dosing schedule. The timing between each dose in a dosing schedule may range between a few hours, six, 12, or 18 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days. The same quantity of protein in the formulation may be administered in each dose of the dosing schedule, or the amounts in each dose may vary. The identity of the particular peptides and polypeptides in the formulation may also vary or remain the same in each dose in a dosing schedule.

The amount of *Staphylococcus aureus* protein administered to a subject in a dose when the methods of the present invention are practiced will vary based on the particular methods being practiced (e.g., prevention versus treatment of a *Staphylococcus aureus* infection), the means and formulation of administration, the age and size of the subject, and the general health of the subject, to name only a few factors to be considered. However, the amount of *Staphylococcus aureus* protein administered to a subject in a dose will be sufficient to induce or boost an immune response in a subject to the components of the vaccine. As an example, an therapeutically effective amount of *Staphylococcus aureus* protein in a dose of a vaccine formulation of the present invention is typically between about 10 to about 200 ug of *Staphylococcus aureus* protein per kg of body weight of the subject to which the dose of the vaccine formulation will be administered.

Appropriate doses and dosing schedules can readily be determined by techniques well known to those of ordinary skill in the art without undue experimentation. Such a determination will be based, in part, on the tolerability and efficacy of a particular dose.

Administration of the vaccine formulations may be via any of the means commonly known in the art of vaccine delivery. Such routes include intravenous, intraperitoneal, intramuscular, subcutaneous and intradermal routes of administration, as well as nasal application, by inhalation, ophthalmically, orally, rectally, vaginally, or by any other mode that results in the vaccine formulation contacting mucosal tissues.

As used herein, the *Staphylococcus aureus* infection may be any *Staphylococcus aureus* of a subject, including, for example, a *Staphylococcus aureus* biofilm infection, a *Staphylococcus aureus* osteomyelitis infection, a biofilm-associated *Staphylococcus aureus* osteomyelitis infection, a *Staphylococcus aureus* indwelling medical device infection, a *Staphylococcus aureus* endocarditis infection, a *Staphylococcus aureus* diabetic wound or ulcer infection, a *Staphylococcus aureus* chronic rhinosinusitis infection, a *Staphylococcus aureus* ventilator associated pneumonia infection, a *Staphylococcus aureus* intravenous catheter associated infection, a *Staphylococcus aureus* skin infection, a *Staphylococcus aureus* nectrotizing fasciitis, a *Staphylococcus aureus* keratitis, a *Staphylococcus aureus* endophthlamitis, a *Staphylococcus aureus* pyopneumothorax, a *Staphylococcus aureus* empyema, and a *Staphylococcus aureus* septicemia.

The term "subject" is intended to mean an animal, such birds or mammals, including humans and animals of veterinary or agricultural importance, such as dogs, cats, horses, sheep, goats, and cattle.

A kit comprising the necessary components of a vaccine formulation that elicits an immune response to a strain of *Staphylococcus aureus* and instructions for its use is also within the purview of the present invention.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

EXAMPLES

Materials and Methods

Unless stated otherwise, the following experimental details pertain to each of the examples provided in the specific Examples set forth and discussed below.

Bacterial strains. MRSA strain MRSA-M2 was isolated from a patient with osteomyelitis at the University of Texas Medical Branch. *Escherichia coli* TOP10 cells were utilized for protein production experiments.

Cloning, expression, and purification of proteins. Candidate antigens selected in Brady et al. (27) were amplified using the primers listed Table 1. The PCR products were cloned into pBAD-Thio/TOPO (SA0037) or pASK-IBA14 (SA0486, SA0688, and glucosaminidase), transformed into TOP10 *E. coli*, and sequenced. The clones were then expressed using either arabinose induction (SA0037) or anhydrotetracycline induction (all others). SA0037 was purified via nickel affinity chromatography while all other antigens were purified using Strep-Tactin Superflow Columns (IBA, Göttingen, Germany). Purity was confirmed by resolving each protein on 15% SDS-PAGE.

TABLE 1

| Primer name | Sequence (5'-3') | Product, size |
| --- | --- | --- |
| 5' SA0037 | ATGAATACAATCAAAACTACGAAA (SEQ ID NO: 5) | Hypothetical protein, 519 bp |
| 3' SA0037 | CTTCTCATCGTCATCTGATTTCAAAATCCATTTTTGA (SEQ ID NO: 6) | |
| 5' Lipase | ACTCTA<u>GGTCTC</u>ACTCCCATCTGAAACAACATTATGACCAAAT (SEQ ID NO: 7) | Lipase, 966 bp |
| 3' Lipase | ATGGTA<u>GGTCTC</u>ATATCATAAAGGATTTAACGGTAATTCATTACT (SEQ ID NO: 8) | |
| 5' SA0688 | ATGGTA<u>GGTCTC</u>ACTCCGATAAGTCAAATGGCAAACTAAAAGT (SEQ ID NO: 9) | ABC trans. lipoprotein, 860 bp |
| 3' SA0688 | ATGGTA<u>GGTCTC</u>ATATCATTTCATGCTTCCGTGTACAGTT (SEQ ID NO: 10) | |
| 5'Glucosaminidase | ATGGTA<u>GGTCTC</u>ACTCCGCTTATACTGTTACTAAACCACAAAC (SEQ ID NO: 11) | Glucosaminidase, 1443 bp |
| 3'Glucosaminidase | ATGGTA<u>GGTCTC</u>ATATCATTTATATTGTGGGATGTCGAAGTATT (SEQ ID NO: 12) | |
| 5' SA0486 | ACTCTA<u>GGTCTC</u>ACTCCAAAGAAGATTCAAAAGAAGAACAAAT (SEQ ID NO: 13) | Hypo. lipoprotein, 683 bp |
| 3' SA0486 | ATGGTA<u>GGTCTC</u>ATATCAGCTATCTTCATCAGACGGCCCA (SEQ ID NO: 14) | |

TABLE 1-continued

| Plasmid | Genotype or Characteristics | Source |
|---|---|---|
| pBAD-Thio/TOPO | 4454 bp<br>pUC ori, Amp$^R$, pBAD promoter, for arabinose-inducible expression of PCR product | Invitrogen Life Technologies |
| pASK-IBA14 | 3001 bp<br>pUC ori, Amp$^R$, tetA promoter, for tetracycline-inducible expression of PCR product | IBA, Göttingen, Germany |

BsaI sites are underlined in primers

Evaluation of antigen expression in *S. aureus* biofilms in vitro. Purified proteins were used to develop polyclonal antibodies through the investigators' laboratory or a commercial source (Lampire, Inc. Everett, Pa.). Antibodies were purified from the serum and used to probe 14 day old *S. aureus* biofilms grown in vitro as described previously (27, 33).

Vaccination of animals. To prepare the purified recombinant proteins for vaccination, the appropriate amounts of SA0037, SA0486, SA0688, and glucosaminidase were combined and TCA precipitated. Because faint extraneous bands in the SA0037 preparation were noticed following purification on the Probond column, a further step of resolving rSA0037 was undertaken, using SDS-PAGE and cutting out of the proper band. This band was then resuspended in 250 µl of PBS, homogenized, and the mixture was used to rehydrate the TCA precipitation. The rehydrated protein was combined with an equal volume of Titermax Gold® adjuvant (Titermax USA, Norcross, Ga.) and mixed via sonication.

Eight-week old female New Zealand White rabbits (2-3 kg each) were used in this study. All procedures were performed as per humane criteria set forth by University of Maryland Baltimore Animal Care and Use Committee. Animals were divided at random into groups. Groups received glucosaminidase, the multi-component vaccine, or PBS as a control. For the initial testing of glucosaminidase as a vaccine candidate, animals were immunized with 10 µg of antigen intramuscularly at days 0, 10, and 20, with challenge following on day 30. In all the remaining other vaccine studies, animals were immunized with 75 µg of antigen intramuscularly with either the vaccine or the PBS control at days 0 and 10. Intratibial inoculation of animals with MRSA was carried out on day 20.

Production of osteomyelitis. Animals were challenged 10 days following the last vaccination with intratibial inoculation of MRSA-M2 as described previously (27, 37, 38). All procedures were performed as per humane criteria set forth by University of Maryland Baltimore Animal Care and Use Committee. The infection was allowed to progress for 14 days.

Figure 4:
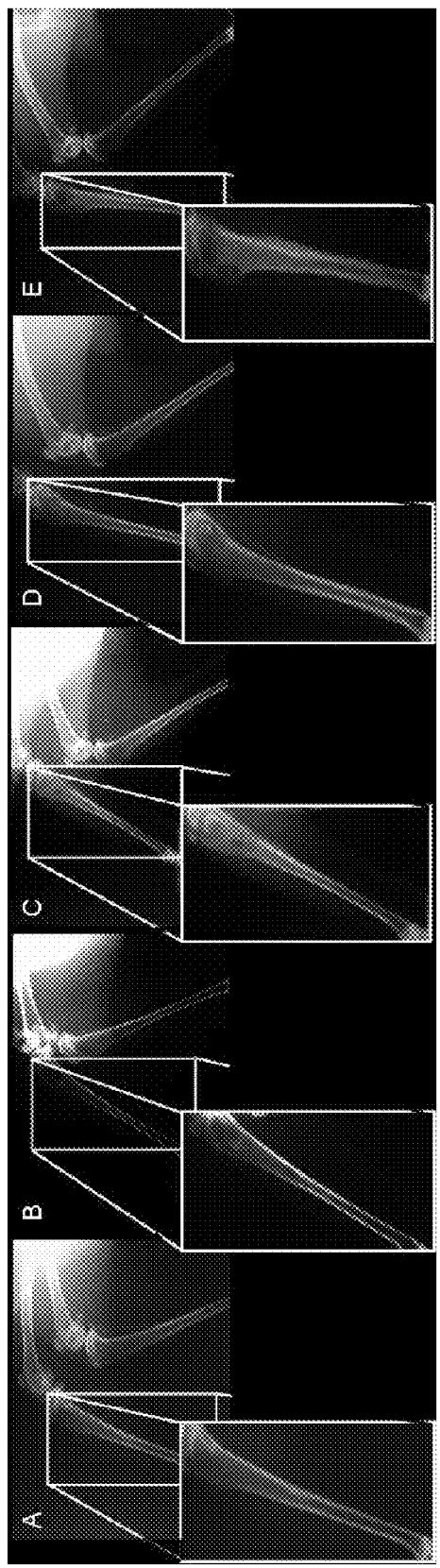
FIG. 4: Radiographic differences between infected and uninfected tibias (A-E). Left tibia of infected rabbits showing a radiographic score of 0-4.

Analysis of vaccine efficacy. Vaccine efficacy was evaluated in three ways. Fourteen days following MRSA inoculation into the tibia, rabbits were monitored for clinical signs of infection (non-weight bearing on the affected leg). Animals were then anesthetized and radiographically examined to determine the radiologic score of osteomyelitis, according to FIG. 4 and described previously (37, 38). Scores were evaluated using the Radiographic Staging Guidelines shown in Table 2. Rabbits were then sacrificed by an intravenous injection of sodium pentobarbital. Both tibias were removed, dissected free of all soft tissue, and processed for bacterial cultures. Using a 5.0 mm, single-action rongeur, the bones were split into small pieces and the marrow was removed. The whole bone was then pulverized, combined with the marrow, and suspended in three ml of sterile 0.85% saline per gram of tissue. Serial ten-fold dilutions were performed in triplicate and spotted onto a tryptic soy agar blood plate supplemented with oxacillin (40 µg/ml) to determine the presence or absence of *S. aureus* in the bone tissue. The colony forming units (CFUs) per gram of bone were then calculated following overnight incubation of the plates at 37° C.

TABLE 2

| Radiological Score | Characteristics of Infected Bone |
|---|---|
| 0 | Normal, no lytic changes around needle stick |
| 1+ | Lytic changes around the needle stick. <5% disruption of normal bone architecture |
| 2+ | 5-15% disruption of normal bone architecture |
| 3+ | 15-40% disruption of normal bone architecture |
| 4+ | >40% disruption of normal bone architecture |

Statistical analysis. Statistical significance was calculated via Student's t test for radiologic and CFU data, and Fisher's Exact Test for clinical symptoms. A p value≦0.05 was considered statistically significant while 0.1>p>0.05 was considered to show a trend.

Example 1

Vaccination with a Single Biofilm Antigen does not Elicit Protection 22 cell wall-associated immunogens were identified in previous work that were up-regulated during biofilm growth (27). Among these antigens, autolysin (AtlA) was one of the most immunoreactive. Because of its reported role in biofilm formation (31, 32) and its up-regulation during early biofilm growth (when an immune response could theoretically eradicate the biofilm), autolysin was tested as a vaccine. Purified recombinant glucosaminidase (one of the two protein components of AtlA) was injected into rabbits (three doses of 10 µg each, 10 days apart) and then animals were challenged using a tibial osteomyelitis infection. This vaccination did not lead to significant differences in bacteriological signs of infection compared to PBS-vaccinated controls but did yield significantly improves radiological scores (Table 3, showing radiological and clinical vaccine scores for glucosaminidase and multi-component vaccines; FIG. 1). As well, no animals in the vaccinated group exhibited limping that would indicate infection.

TABLE 3

| | Glucosaminidase | Multi-component | PBS Control |
|---|---|---|---|
| Number of rabbits | 4 | 5 | 7 |
| Mean radiological score | 0.37* | 1.10* | 2.71 |

TABLE 3-continued

|  | Glucosaminidase | Multi-component | PBS Control |
|---|---|---|---|
| % showing clinical signs of infection | 0% | 0% | 57% |
| Number cleared | 1 | 0 | 0 |

*$p < 0.05$ Glucosaminidase vs. PBS Control and Multi-component vs. PBS Control.

The failure of this antigen to promote effective bacterial clearance may have been due to the inability of the immune system to clear planktonic cells, since the antigen was a biofilm up-regulated protein. In addition, differential protein production within the biofilm may have allowed certain portions of the biofilm to escape immune recognition and clearance. Therefore, a broader subset of candidate antigens was chosen for study. These included the already studied glucosaminidase as well as SA0486, a hypothetical lipoprotein, SA0037, a conserved hypothetical protein of unknown function, and SA0688, an ABC transporter lipoprotein. These other antigens were chosen because it was shown in earlier work (27) that they are cell wall-associated, biofilm-specific, and immunogenic in the rabbit.

Example 2

Biofilm-Specific Immunogens are Produced Heterogeneously within the Biofilm

Figure 2:
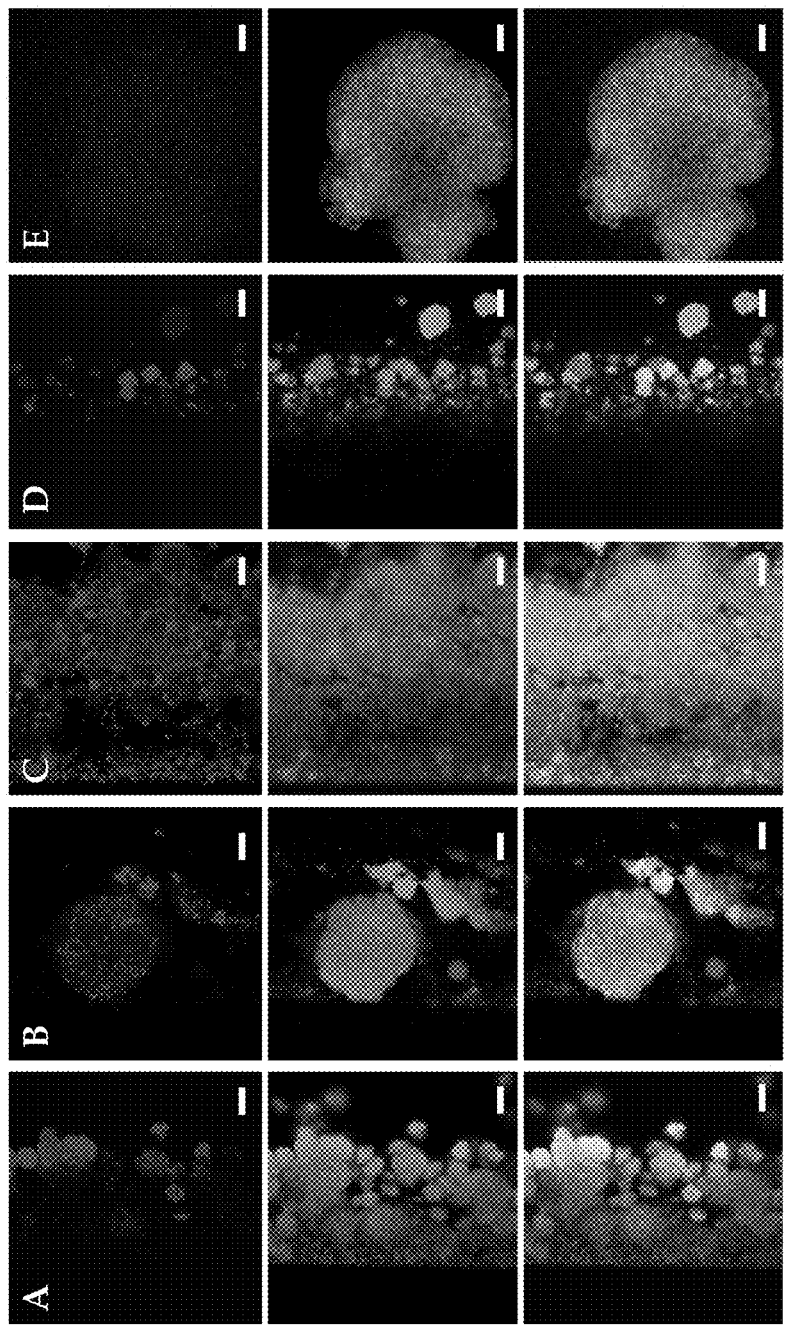
FIG. 2: Biofilm-specific immunogens are produced heterogeneously. Immunofluorescence microscopy was employed using IgG antibodies against biofilm-specific immunogens followed by goat anti-rabbit $F(ab')_2$ secondary antibody (red, top panels) and SYTO-9 stain to visualize the entire biofilm (green, center panels; merge, bottom panels). (A) Glucosaminidase; (B) SA0486; (C) SA0688; (D) SA0037; (E) lipase, a secreted protein not found in large quantities within the biofilm (negative control). Magnification bars=20 µm.

IgG samples from animals vaccinated against the individual antigens were used with confocal immunofluorescence microscopy on *S. aureus* biofilms grown in vitro to determine the relative areas of production a number of other biofilm up-regulated antigens. As was seen in previous studies (33), there was heterogeneous production of proteins within the biofilm community (FIG. 2). IgG against each biofilm up-regulated antigen appears to bind to *S. aureus* biofilms differently. While anti-glucosaminidase and anti-SA0688 IgGs bind to individual microcolonies, anti-SA0486 IgG reacts with smaller bacterial flocs within the entire biofilm, and anti-SA0037 IgG binds to individual cells within microcolonies. In addition, the negative control antigen lipase, which is secreted by *S. aureus* in a biofilm mode of growth, showed no biofilm localization of anti-lipase IgG. Thus it was evident that the tested antigens are not expressed homogeneously throughout the biofilm and that antibodies to a single antigen may not provide adequate immunological recognition of the biofilm, leaving some areas that were not recognized and thus permitted persistence.

Example 3

Figure 3:
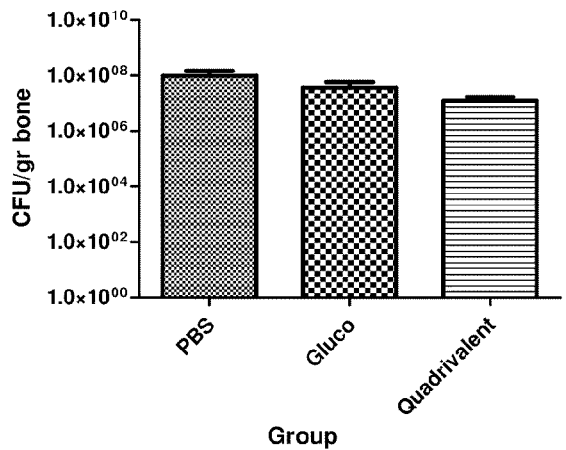
FIG. 3: Vaccination with quadrivalent vaccine. (A) Animals vaccinated with three doses of the quadrivalent vaccine (10 µg each) or PBS. (B) Animals vaccinated with PBS only (1), PBS and subsequent treatment with vancomycin (2), the multi-component vaccine only (3), or the vaccine plus vancomycin (4). *=significant difference from group 1 (p<0.05, student's T test). (C) Animals in each group that were completely cleared of infection. *=significant difference from group 1 (p<0.05, Fisher's Exact Test).
Figure 3:
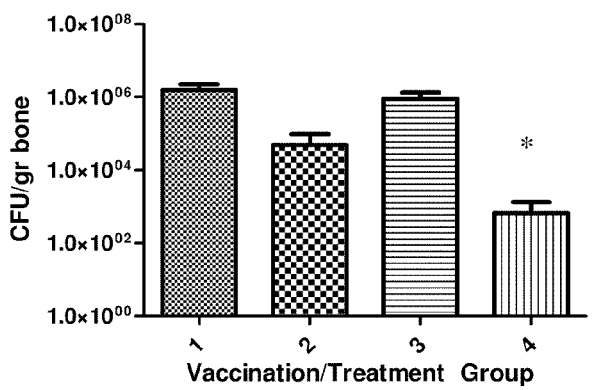
Figure 3:
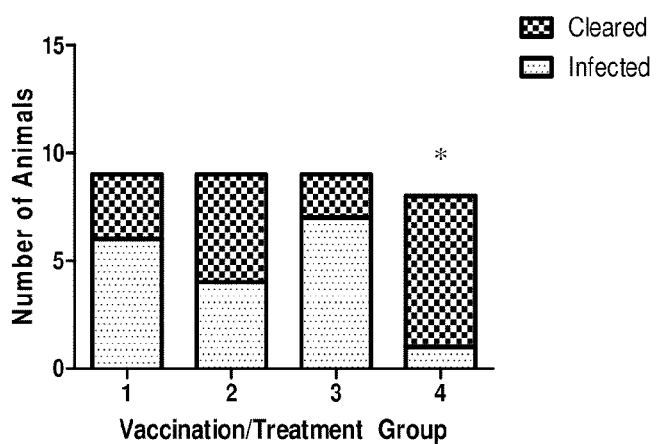

Vaccination with a Multi-Component S. aureus Biofilm Vaccine Leads to Increased S. aureus Clearance During Tibial Osteomyelitis Antibodies elicited by a single antigen vaccine may not provide adequate immunological recognition of the biofilm in vivo to enable complete microbial clearance. In addition, other work (26) has shown that antigens were more effective in preventing disease when they were combined than when they were administered individually. Therefore, the aforementioned antigens were tested as a multi-component vaccine. To this end, animals were vaccinated with 10 µg of each of four antigens: glucosaminidase, SA0688 (an ABC transporter lipoprotein), SA0037 (a conserved hypothetical protein), and SA0486 (a hypothetical lipoprotein), following the same dosing schedule as above. Upon challenge, animals showed improved status, with significantly lower radiological scores and no animals exhibiting clinical symptoms (Table 3). As well, vaccinated animals trended to lower CFU counts and an 88% reduction in bacterial loads in the tibia (FIG. 3A—quadrivalent). However, this reduction in bacterial populations was not statistically significant. Two doses of the combined vaccine at 15 µg each per dose were also studied, wherein increasing the prime and boost may lead to a more robust initial immune response when the biofilm is immature (and thus, enable clearance by the immune response). However, no significant differences with respect to bacterial loads and clearance levels between vaccinated and control animals were found under these conditions (data not shown).

Though the bacterial counts presented here were lower than controls, they were still not statistically significant. However, this vaccine does elicit reduction in levels consistent with other works. When Maira-Litran et al. (14) tested their deacetylated PNAG vaccine in a murine bacteremia model, they saw bacterial levels that were 55-91% lower than in controls. Another potential vaccine, the StaphVAX™ capsule conjugate vaccine, affords only 60% protection (34) and, by one year post-vaccination, protection wanes to 30% (11). In a study of ClfA vaccines, vaccination with rClfA did lessen the degree of damage in a septic arthritis model; however, 33%-92% of vaccinated animals still showed signs of infection (19). Kuklin et al. (22) showed only approximately 40% increased survival in a murine sepsis model upon vaccination with recombinant IsdB. Thus, an 88% reduction in CFU levels, along with decreases in both damage to the bone and clinical signs of infection, is similar with the results seen elsewhere. In addition, this is the only study to use a biofilm model of disease.

Example 4

Vaccination with Biofilm-Specific Antigens, and Subsequent Antimicrobial Agent Therapy, Leads to Clearance of Biofilm Infection Although similar bacterial population reductions were seen in the studies mentioned above, the ultimate goal of complete bacterial clearance was not realized with the multi-component vaccine. Because there was an obvious, albeit non-statistically significant trend to reduced infection upon challenge with the multi-component vaccine, it was hypothesized that vaccination with these biofilm-specific antigens may reduce the number of bacterial cells with a biofilm phenotype. As a result, the bacterial populations remaining in the vaccinated group post challenge may be due to the planktonic populations within the tibia escaping clearance by the host immune response.

Planktonic *S. aureus* cells possess a number of immuno-avoidance strategies, including protein A, leukotoxin, an antiphagocytic capsule, and the recently described phenol soluble modulins and nitric oxide inducible lactate dehydrogenase system (35, 36) that enable persistence. However, they are sensitive to effective antimicrobial agents compared to their biofilm-embedded counterparts.

To this end, 14 days following challenge both vaccinated and non-vaccinated animals were treated with 40 mg/kg vancomycin twice daily for ten days, and efficacy of the dual treatment was compared to untreated and unvaccinated, vaccinated but untreated, and unvaccinated but treated controls. The dose of antigens was also increased to 75 µg each per injection in order to increase the hosts' response levels. As in the studies described above, the increased vaccine dose alone showed no significant effect on infection clearance or concentrations of bacteria in the tibia (FIG. 3B). However, the addition of vancomycin therapy following vaccination with the quadrivalent vaccine was able to significantly reduce bacterial counts in the affected tibia (P<0.05, Student's t test). Importantly, only one out of the eight vaccinated and treated animals had any detectable *S. aureus* in the tibia, and its level was significantly lower compared to the mean CFUs in control animals (>3 log difference) (P<0.05, Fisher's Exact Test) (Table 4 and FIG. 3C). This treatment also afforded significantly lower scores for clinical and radiological signs of disease compared to unvaccinated, untreated controls (Table 4 and FIG. 4). This is not surprising since clinical and radiological signs of osteomyelitis often lag up to 2 weeks behind disease resolution.

TABLE 4

|  | 1 (PBS) | 2 (PBS + vancomycin) | 3 (Vaccine) | 4 (Vaccine + vancomycin) |
|---|---|---|---|---|
| Number of rabbits | 9 | 9 | 9 | 8 |
| Mean radiological score | 2.3 | 2.1 | 2.0 | 0.4* |
| Percentage showing clinical signs of infection | 100% | 100% | 66% | 38%* |
| Number cleared | 3 | 5 | 2 | 7* |

*p < 0.05 of Vaccine + Vancomycin Group 4 vs. PBS Control Group 1

Thus, this combination therapy was able to significantly clear *S. aureus* osteomyelitis infections, and in the rare case where clearance was not achieved, bacterial levels (as well as severity of disease) were markedly decreased. Thus, the combination of prophylactic, biofilm-specific vaccine plus antimicrobial agent treatment aimed at planktonic growth leads to abrogation of biofilm-mediated osteomyelitis infection in a rabbit model.

REFERENCES

1. R. M. Klevens et al., *JAMA*. 298, 1763 (2007).
2. T. C. Horan et al., *Infect. Control Hosp. Epidemiol.* 14, 73 (1993).
3. J. M. Boyce, G. Potter-Bynoe, L. Dziobek, *Infect. Control Hosp. Epidemiol.* 11, 89 (1990).
4. J. M. Boyce, L. Dziobek, G. Potter-Bynoe, *Ann. Intern. Med.* 108, 776 (1988).
5. J. A. Lindsay, M. T. Holden, *Trends Microbiol* 12, 378 (2004).
6. B. M. Benton et al., *J. Bacteriol.* 186, 8478 (2004).
7. D. L. Watson, *Vaccine.* 5, 275 (1987).
8. D. L. Watson, C. G. Lee, *Aust. Vet. J.* 54, 374 (1978).
9. R. D. Arbeit, W. W. Karakawa, W. F. Vann, J. B. Robbins, *Diagn. Microbiol. Infect. Dis.* 2, 85 (1984).
10. A. I. Fattom, G. Horwith, S. Fuller, M. Propst, R. Naso, *Vaccine.* 22, 880 (2004).
11. H. Shinefield et al., *N. Engl. J. Med.* 346, 491 (2002).
12. D. McKenney et al., *Science* 284, 1523 (1999).
13. T. Maira-Litran et al., *Infect. Immun.* 70, 4433 (2002).
14. T. Maira-Litran, A. Kropec, D. A. Goldmann, G. B. Pier, *Infect. Immun.* 73, 6752 (2005).
15. H. Rohde et al., *Biomaterials.* 28, 1711 (2007).
16. A. Nilsdotter-Augustinsson, A. Koskela, L. Ohman, B. Soderquist, *Eur. J. Clin. Microbiol. Infect. Dis.* 26, 255 (2007).
17. F. Fitzpatrick, H. Humphreys, J. P. O'Gara, *J. Clin. Microbiol.* 43, 1973 (2005).
18. E. O'neill et al., *J. Clin. Microbiol.*, 1379 (2007).
19. E. Josefsson, O. Hartford, L. O'Brien, J. M. Patti, T. Foster, *J. Infect. Dis.* 184, 1572 (2001).
20. E. Brouillette et al., *Vaccine* 20, 2348 (2002).
21. A. C. Schaffer et al., *Infect. Immun.* 74, 2145 (2006).
22. N. A. Kuklin et al., *Infect. Immun.* 74, 2215 (2006).
23. H. Zhou, Z. Y. Xiong, H. P. Li, Y. L. Zheng, Y. Q. Jiang, *Vaccine.* 24, 4830 (2006).
24. E. D. Ni et al., *Mol. Microbiol.* 30, 245 (1998).
25. U. Ryding, J. I. Flock, M. Flock, B. Soderquist, B. Christensson, *J. Infect. Dis.* 176, 1096 (1997).
26. Y. K. Stranger-Jones, T. Bae, O, Schneewind, *Proc. Natl. Acad. Sci. U.S.A.* 103, 16942 (2006).
27. R. A. Brady, J. G. Leid, A. K. Camper, J. W. Costerton, Shirtliff M. E., *Infect. Immun.* 74, 3415 (2006).
28. P. Becker, W. Hufnagle, G. Peters, M. Herrmann, *Appl. Environ. Microbiol.* 67, 2958 (2001).
29. K. E. Beenken et al., *J. Bacteriol.* 186, 4665 (2004).
30. A. Resch, R. Rosenstein, C. Nerz, F. Gotz, *Appl. Environ. Microbiol.* 71, 2663 (2005).
31. C. Heilmann, M. Hussain, G. Peters, F. Gotz, *Mol. Microbiol.* 24, 1013 (1997).
32. R. Biswas et al., *FEMS Microbiol. Lett.* 259, 260 (2006).
33. R. A. Brady, J. G. Leid, J. Kofonow, J. W. Costerton, M. E. Shirtliff, *Appl Environ Microbiol.* 73, 6612 (2007).
34. A. Fattom et al., *Vaccine* 23, 656 (2004).
35. R. M. Klevens et al., *JAMA.* 298, 1763 (2007).
36. A. R. Richardson, S. J. Libby, F. C. Fang, *Science.* 319, 1672 (2008).
37. J. T. Mader, M. E. Shirtliff, in *Handbook of Animal Models of Infection*, O. Zak, M. A. Sande, Eds. (Academic Press Ltd., London, England, 1999), pp. 581-591.
38. M. E. Shirtliff, J. H. Calhoun, J. T. Mader, *J. Antimicrob. Chemother.* 48, 253 (2001).

What is claimed is:

1. A vaccine formulation comprising:
   (a) four *Staphylococcus aureus* polypeptides, wherein the *Staphylococcus aureus* polypeptides are (i) glucosaminidase as set forth in SEQ ID NO:1, (ii) SA0688 as set forth in SEQ ID NO:2, (iii) SA0037 as set forth in SEQ ID NO:3, and (iv) SA0486 as set forth in SEQ ID NO:4, and
   (b) a pharmaceutically acceptable carrier or diluent.

2. A method of inhibiting a *Staphylococcus aureus* infection in a subject, comprising administering a therapeutically effective amount of a vaccine formulation of claim 1 to a subject at risk of developing a *Staphylococcus aureus* infection, thereby inhibiting a *Staphylococcus aureus* infection in a subject.

3. The method of claim 2, further comprising administering an antimicrobial agent to the subject, wherein the antimicrobial agent is administered before, concurrent with, or after the vaccine formulation.

4. The method of claim 3, wherein the antimicrobial agent is selected from the group consisting of an aminoglycoside, a carbacephem, a carbapenem, a cephalosporin, a glycopeptide, a macrolide, a monobactam, a penicillin, a polypeptide, a quinolone, a sulfonamide, a tetracycline, chloramphenicol, clindamycin, lincomycin, fusidic acid, furazolidone, linezolid, metronidazole, mupirocin, nitrofurantoin, macrobid, platensimycin, quinupristin/dalfopristin, rifampin and rifampicin.

5. The method of claim 2, wherein the *Staphylococcus aureus* infection is selected from the group consisting of a *Staphylococcus aureus* biofilm infection, a *Staphylococcus aureus* osteomyelitis infection and a biofilm-associated *Staphylococcus aureus* osteomyelitis infection.

* * * * *

SEQUENCE LISTING

<160> NUMBER OF SEQ ID NOS: 14

<210> SEQ ID NO 1
<211> LENGTH: 1257
<212> TYPE: PRT
<213> ORGANISM: Staphylococcus aureus

<400> SEQUENCE: 1

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val
            35                  40                  45

Lys Ala Thr Thr Glu Gln Ala Lys Ala Glu Val Lys Asn Pro Thr Gln
 50                  55                  60

Asn Ile Ser Gly Thr Gln Val Tyr Gln Asp Pro Ala Ile Val Gln Pro
 65                  70                  75                  80

Lys Ala Ala Asn Lys Thr Gly Asn Ala Gln Val Asn Gln Lys Val Asp
                 85                  90                  95

Thr Thr Gln Val Asn Gly Asp Thr Arg Ala Thr Gln Ser Thr Thr Ser
             100                 105                 110

Asn Asn Ala Lys Pro Val Thr Lys Ser Thr Asn Thr Thr Ala Pro Lys
             115                 120                 125

Thr Asn Asn Val Thr Ser Ala Gly Tyr Ser Leu Val Asp Asp Glu
             130                 135                 140

Asp Asp Asn Ser Glu Asn Gln Ile Asn Pro Glu Leu Ile Lys Ser Ala
145                 150                 155                 160

Ala Lys Pro Ala Ala Leu Glu Thr Gln Tyr Lys Ala Ala Pro Lys
             165                 170                 175

Ala Thr Pro Val Ala Pro Lys Ala Lys Thr Glu Ala Thr Pro Lys Val
             180                 185                 190

Thr Thr Phe Ser Ala Ser Ala Gln Pro Arg Ser Ala Ala Ala Pro
             195                 200                 205

Lys Thr Ser Leu Pro Lys Tyr Lys Pro Gln Val Asn Ser Ser Ile Asn
             210                 215                 220

Asp Tyr Ile Arg Lys Asn Asn Leu Lys Ala Pro Lys Ile Glu Glu Asp
225                 230                 235                 240

Tyr Thr Ser Tyr Phe Pro Lys Tyr Ala Tyr Arg Asn Gly Val Gly Arg
             245                 250                 255

Pro Glu Gly Ile Val Val His Asp Thr Ala Asn Asp Arg Ser Thr Ile
             260                 265                 270

Asn Gly Glu Ile Ser Tyr Met Lys Asn Asn Tyr Gln Asn Ala Phe Val
             275                 280                 285

His Ala Phe Val Asp Gly Asp Arg Ile Ile Glu Thr Ala Pro Thr Asp
             290                 295                 300

Tyr Leu Ser Trp Gly Val Gly Ala Val Gly Asn Pro Arg Phe Ile Asn
305                 310                 315                 320

Val Glu Ile Val His Thr His Asp Tyr Ala Ser Phe Ala Arg Ser Met
                 325                 330                 335

Asn Asn Tyr Ala Asp Tyr Ala Ala Thr Gln Leu Gln Tyr Tyr Gly Leu
             340                 345                 350

Lys Pro Asp Ser Ala Glu Tyr Asp Gly Asn Gly Thr Val Trp Thr His
             355                 360                 365

Tyr Ala Val Ser Lys Tyr Leu Gly Gly Thr Asp His Ala Asp Pro His
 370                 375                 380

Gly Tyr Leu Arg Ser His Asn Tyr Ser Tyr Asp Gln Leu Tyr Asp Leu
385                 390                 395                 400

Ile Asn Glu Lys Tyr Leu Ile Lys Met Gly Lys Val Ala Pro Trp Gly
                 405                 410                 415

Thr Gln Ser Thr Thr Pro Thr Pro Ser Lys Pro Ser Thr Pro
             420                 425                 430

Ser Lys Pro Ser Thr Pro Ser Thr Gly Lys Leu Thr Val Ala Ala Asn
             435                 440                 445

Asn Gly Val Ala Gln Ile Lys Pro Thr Asn Ser Gly Leu Tyr Thr Thr

```
                450             455             460
Val Tyr Asp Lys Thr Gly Lys Ala Thr Asn Glu Val Gln Lys Thr Phe
465                 470                 475                 480

Ala Val Ser Lys Thr Ala Thr Leu Gly Asn Gln Lys Phe Tyr Leu Val
                485                 490                 495

Gln Asp Tyr Asn Ser Gly Asn Lys Phe Gly Trp Val Lys Glu Gly Asp
                500                 505                 510

Val Val Tyr Asn Thr Ala Lys Ser Pro Val Asn Val Gln Ser Tyr
                515                 520                 525

Ser Ile Lys Pro Gly Thr Lys Leu Tyr Thr Val Pro Trp Gly Thr Ser
530                 535                 540

Lys Gln Val Ala Gly Ser Val Ser Gly Ser Asn Gln Thr Phe Lys
545                 550                 555                 560

Ala Ser Lys Gln Gln Gln Ile Asp Lys Ser Ile Tyr Leu Tyr Gly Ser
                565                 570                 575

Val Asn Gly Lys Ser Gly Trp Val Ser Lys Ala Tyr Leu Val Asp Thr
                580                 585                 590

Ala Lys Pro Thr Pro Thr Pro Thr Pro Lys Pro Ser Thr Pro Thr Thr
                595                 600                 605

Asn Asn Lys Leu Thr Val Ser Ser Leu Asn Gly Val Ala Gln Ile Asn
                610                 615                 620

Ala Lys Asn Asn Gly Leu Phe Thr Thr Val Tyr Asp Lys Thr Gly Lys
625                 630                 635                 640

Pro Thr Lys Glu Val Gln Lys Thr Phe Ala Val Thr Lys Glu Ala Ser
                645                 650                 655

Leu Gly Gly Asn Lys Phe Tyr Leu Val Lys Asp Tyr Asn Ser Pro Thr
                660                 665                 670

Leu Ile Gly Trp Val Lys Gln Gly Asp Val Ile Tyr Asn Asn Ala Lys
                675                 680                 685

Ser Pro Val Asn Val Met Gln Thr Tyr Thr Val Lys Pro Gly Thr Lys
                690                 695                 700

Leu Tyr Ser Val Pro Trp Gly Thr Tyr Lys Gln Glu Ala Gly Ala Val
705                 710                 715                 720

Ser Gly Thr Gly Asn Gln Thr Phe Lys Ala Thr Lys Gln Gln Gln Ile
                725                 730                 735

Asp Lys Ser Ile Tyr Leu Tyr Gly Thr Val Asn Gly Lys Ser Gly Trp
                740                 745                 750

Ile Ser Lys Ala Tyr Leu Ala Val Pro Ala Ala Pro Lys Lys Ala Val
                755                 760                 765

Ala Gln Pro Lys Thr Ala Val Lys Ala Tyr Ala Val Thr Lys Pro Gln
770                 775                 780

Thr Thr Gln Thr Val Ser Lys Ile Ala Gln Val Lys Pro Asn Asn Thr
785                 790                 795                 800

Gly Ile Arg Ala Ser Val Tyr Glu Lys Thr Ala Lys Asn Gly Ala Lys
                805                 810                 815

Tyr Ala Asp Arg Thr Phe Tyr Val Thr Lys Glu Arg Ala His Gly Asn
                820                 825                 830

Glu Thr Tyr Val Leu Leu Asn Asn Thr Ser His Asn Ile Pro Leu Gly
                835                 840                 845

Trp Phe Asn Val Lys Asp Leu Asn Val Gln Asn Leu Gly Lys Glu Val
                850                 855                 860

Lys Thr Thr Gln Lys Tyr Thr Val Asn Arg Ser Asn Asn Gly Leu Ser
865                 870                 875                 880
```

```
Met Val Pro Trp Gly Thr Lys Asn Gln Val Ile Leu Thr Gly Asn Asn
                885                 890                 895

Ile Ala Gln Gly Thr Phe Asn Ala Thr Lys Gln Val Ser Val Gly Lys
            900                 905                 910

Asp Val Tyr Leu Tyr Gly Thr Ile Asn Asn Arg Thr Gly Trp Val Asn
        915                 920                 925

Ser Lys Asp Leu Thr Ala Pro Thr Ala Val Lys Pro Thr Thr Ser Ala
    930                 935                 940

Ala Lys Asp Tyr Asn Tyr Thr Tyr Val Ile Lys Asn Gly Asn Gly Tyr
945                 950                 955                 960

Tyr Tyr Val Thr Pro Asn Ser Asp Thr Ala Lys Tyr Ser Leu Lys Ala
                965                 970                 975

Phe Asn Glu Gln Pro Phe Ala Val Val Lys Glu Gln Val Ile Asn Gly
            980                 985                 990

Gln Thr Trp Tyr Tyr Gly Lys Leu  Ser Asn Gly Lys Leu  Ala Trp Ile
        995                 1000                1005

Lys Ser  Thr Asp Leu Ala Lys  Glu Leu Ile Lys Tyr  Asn Gln Ile
    1010                1015                1020

Gly Met  Thr Leu Asn Gln Val  Ala Gln Ile Gln Ala  Gly Leu Gln
    1025                1030                1035

Tyr Lys  Pro Gln Val Gln Arg  Val Pro Gly Lys Trp  Thr Asp Ala
    1040                1045                1050

Asn Phe  Asn Asp Val Lys His  Ala Met Asp Thr Lys  Arg Leu Ala
    1055                1060                1065

Gln Asp  Pro Ala Leu Lys Tyr  Gln Phe Leu Arg Leu  Asp Gln Pro
    1070                1075                1080

Gln Asn  Ile Ser Ile Asp Lys  Ile Asn Gln Phe Leu  Lys Gly Lys
    1085                1090                1095

Gly Val  Leu Glu Asn Gln Gly  Ala Ala Phe Asn Lys  Ala Ala Gln
    1100                1105                1110

Met Tyr  Gly Ile Asn Glu Val  Tyr Leu Ile Ser His  Ala Leu Leu
    1115                1120                1125

Glu Thr  Gly Asn Gly Thr Ser  Gln Leu Ala Lys Gly  Ala Asp Val
    1130                1135                1140

Val Asn  Asn Lys Val Val Thr  Asn Ser Asn Thr Lys  Tyr His Asn
    1145                1150                1155

Val Phe  Gly Ile Ala Ala Tyr  Asp Asn Asp Pro Leu  Arg Glu Gly
    1160                1165                1170

Ile Lys  Tyr Ala Lys Gln Ala  Gly Trp Asp Thr Val  Ser Lys Ala
    1175                1180                1185

Ile Val  Gly Gly Ala Lys Phe  Ile Gly Asn Ser Tyr  Val Lys Ala
    1190                1195                1200

Gly Gln  Asn Thr Leu Tyr Lys  Met Arg Trp Asn Pro  Ala His Pro
    1205                1210                1215

Gly Thr  His Gln Tyr Ala Thr  Asp Val Asp Trp Ala  Asn Ile Asn
    1220                1225                1230

Ala Lys  Ile Ile Lys Gly Tyr  Tyr Asp Lys Ile Gly  Glu Val Gly
    1235                1240                1245

Lys Tyr  Phe Asp Ile Pro Gln  Tyr Lys
    1250                1255

<210> SEQ ID NO 2
<211> LENGTH: 309
<212> TYPE: PRT
<213> ORGANISM: Staphylococcus aureus
```

-continued

```
<400> SEQUENCE: 2

Met Lys Lys Leu Val Pro Leu Leu Leu Ala Leu Leu Leu Val Ala
1               5                   10                  15

Ala Cys Gly Thr Gly Gly Lys Gln Ser Ser Asp Lys Ser Asn Gly Lys
                20                  25                  30

Leu Lys Val Val Thr Thr Asn Ser Ile Leu Tyr Asp Met Ala Lys Asn
                35                  40                  45

Val Gly Gly Asp Asn Val Asp Ile His Ser Ile Val Pro Val Gly Gln
            50                  55                  60

Asp Pro His Glu Tyr Glu Val Lys Pro Lys Asp Ile Lys Lys Leu Thr
65              70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110

Lys Lys Val Ile Ala Val Ser Lys Asp Val Lys Pro Ile Tyr Leu Asn
                115                 120                 125

Gly Glu Glu Gly Asn Lys Asp Lys Gln Asp Pro His Ala Trp Leu Ser
130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
                180                 185                 190

Asn Asp Ile Pro Lys Glu Gln Arg Ala Met Ile Thr Ser Glu Gly Ala
                195                 200                 205

Phe Lys Tyr Phe Ser Lys Gln Tyr Gly Ile Thr Pro Gly Tyr Ile Trp
            210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
                260                 265                 270

Asp Ile Phe Gly Glu Val Tyr Thr Asp Ser Ile Gly Lys Glu Gly Thr
                275                 280                 285

Lys Gly Asp Ser Tyr Tyr Lys Met Met Lys Ser Asn Ile Glu Thr Val
                290                 295                 300

His Gly Ser Met Lys
305

<210> SEQ ID NO 3
<211> LENGTH: 168
<212> TYPE: PRT
<213> ORGANISM: Staphylococcus aureus

<400> SEQUENCE: 3

Met Asn Thr Ile Lys Asn Thr Ile Tyr Thr Glu Ala Ile Phe Ser Lys
1               5                   10                  15

Asp Glu Lys His Arg Tyr Leu Leu Lys Lys Thr Trp Asp Glu Lys Lys
                20                  25                  30

Pro Ala Cys Thr Val Ile Thr Met Tyr Pro His Leu Asp Gly Val Leu
                35                  40                  45
```

```
Ser Leu Asp Leu Thr Thr Val Leu Ile Leu Asn Gln Leu Ala Asn Ser
        50                  55                  60

Glu Arg Tyr Gly Ala Val Tyr Leu Val Asn Leu Phe Ser Asn Ile Lys
 65                  70                  75                  80

Thr Pro Glu Asn Leu Lys His Ile Lys Glu Pro Tyr Asp Lys His Thr
                 85                  90                  95

Asp Ile His Leu Met Lys Ala Ile Ser Glu Ser Asp Thr Val Ile Leu
                100                 105                 110

Ala Tyr Gly Ala Tyr Ala Lys Arg Pro Val Val Glu Arg Val Glu
                115                 120                 125

Gln Val Met Glu Met Leu Lys Pro His Lys Lys Val Lys Lys Leu
        130                 135                 140

Ile Asn Pro Ala Thr Asn Glu Ile Met His Pro Leu Asn Pro Lys Ala
145                 150                 155                 160

Arg Gln Lys Trp Thr Leu Lys Ala
                165
```

<210> SEQ ID NO 4
<211> LENGTH: 270
<212> TYPE: PRT
<213> ORGANISM: Staphylococcus aureus

<400> SEQUENCE: 4

```
Met Lys Tyr Lys Thr Glu Arg Arg Glu Met Met Gly Asn Ile Lys Ser
 1               5                  10                  15

Phe Ala Leu Tyr Ile Ser Ile Leu Leu Leu Ile Val Val Val Ala Gly
                 20                  25                  30

Cys Gly Lys Ser Asp Lys Thr Lys Glu Asp Ser Lys Glu Glu Gln Ile
                 35                  40                  45

Lys Lys Ser Phe Ala Lys Thr Leu Asp Met Tyr Pro Ile Lys Asn Leu
 50                  55                  60

Glu Asp Leu Tyr Asp Lys Glu Gly Tyr Arg Asp Gly Glu Phe Lys Lys
 65                  70                  75                  80

Gly Asp Lys Gly Thr Trp Thr Leu Leu Thr Ser Phe Ser Lys Ser Asn
                 85                  90                  95

Lys Pro Asp Glu Ile Asp Asp Glu Gly Met Val Leu Tyr Leu Asn Arg
                100                 105                 110

Asn Thr Lys Lys Ala Thr Gly Tyr Tyr Phe Val Asn Lys Ile Tyr Asp
                115                 120                 125

Asp Ile Ser Lys Asn Gln Asn Gly Lys Lys Tyr Arg Val Glu Leu Lys
                130                 135                 140

Asn Asn Lys Ile Val Leu Leu Asp Asn Val Glu Asp Glu Lys Leu Lys
145                 150                 155                 160

Gln Lys Ile Glu Asn Phe Lys Phe Phe Ser Gln Tyr Ala Asp Phe Lys
                165                 170                 175

Asp Leu Lys Asn Tyr Gln Asp Gly Ser Ile Thr Thr Asn Glu Asn Ile
                180                 185                 190

Pro Ser Tyr Glu Ala Glu Tyr Lys Leu Asn Asn Ser Asp Glu Asn Val
                195                 200                 205

Lys Lys Leu Arg Asp Ile Tyr Pro Ile Thr Lys Lys Ala Pro Ile
210                 215                 220

Leu Lys Leu His Ile Asp Gly Asp Ile Lys Gly Ser Ser Val Gly Tyr
225                 230                 235                 240

Lys Lys Ile Glu Tyr Lys Phe Ser Lys Val Lys Asp Gln Glu Thr Thr
                245                 250                 255
```

Leu Arg Asp Tyr Leu Asn Phe Gly Pro Ser Asp Glu Asp Ser
                260                 265                 270

<210> SEQ ID NO 5
<211> LENGTH: 24
<212> TYPE: DNA
<213> ORGANISM: Artificial Sequence
<220> FEATURE:
<223> OTHER INFORMATION: chemically-synthesized PCR primer

<400> SEQUENCE: 5
atgaatacaa tcaaaactac gaaa                                          24

<210> SEQ ID NO 6
<211> LENGTH: 37
<212> TYPE: DNA
<213> ORGANISM: Artificial Sequence
<220> FEATURE:
<223> OTHER INFORMATION: chemically-synthesized PCR primer

<400> SEQUENCE: 6
cttctcatcg tcatctgatt tcaaaatcca tttttga                            37

<210> SEQ ID NO 7
<211> LENGTH: 43
<212> TYPE: DNA
<213> ORGANISM: Artificial Sequence
<220> FEATURE:
<223> OTHER INFORMATION: chemically-synthesized PCR primer

<400> SEQUENCE: 7
actctaggtc tcactcccat ctgaaacaac attatgacca aat                     43

<210> SEQ ID NO 8
<211> LENGTH: 45
<212> TYPE: DNA
<213> ORGANISM: Artificial Sequence
<220> FEATURE:
<223> OTHER INFORMATION: chemically-synthesized PCR primer

<400> SEQUENCE: 8
atggtaggtc tcatatcata aaggatttaa cggtaattca ttact                   45

<210> SEQ ID NO 9
<211> LENGTH: 43
<212> TYPE: DNA
<213> ORGANISM: Artificial Sequence
<220> FEATURE:
<223> OTHER INFORMATION: chemically-synthesized PCR primer

<400> SEQUENCE: 9
atggtaggtc tcactccgat aagtcaaatg gcaaactaaa agt                     43

<210> SEQ ID NO 10
<211> LENGTH: 40
<212> TYPE: DNA
<213> ORGANISM: Artificial Sequence
<220> FEATURE:
<223> OTHER INFORMATION: chemically-synthesized PCR primer

<400> SEQUENCE: 10
atggtaggtc tcatatcatt tcatgcttcc gtgtacagtt                         40

<210> SEQ ID NO 11
<211> LENGTH: 43
<212> TYPE: DNA
<213> ORGANISM: Artificial Sequence

```
-continued

<220> FEATURE:
<223> OTHER INFORMATION: chemically-synthesized PCR primer

<400> SEQUENCE: 11
atggtaggtc tcactccgct tatactgtta ctaaaccaca aac                    43

<210> SEQ ID NO 12
<211> LENGTH: 44
<212> TYPE: DNA
<213> ORGANISM: Artificial Sequence
<220> FEATURE:
<223> OTHER INFORMATION: chemically-synthesized PCR primer

<400> SEQUENCE: 12
atggtaggtc tcatatcatt tatattgtgg gatgtcgaag tatt                   44

<210> SEQ ID NO 13
<211> LENGTH: 43
<212> TYPE: DNA
<213> ORGANISM: Artificial Sequence
<220> FEATURE:
<223> OTHER INFORMATION: chemically-synthesized PCR primer

<400> SEQUENCE: 13
actctaggtc tcactccaaa gaagattcaa aagaagaaca aat                    43

<210> SEQ ID NO 14
<211> LENGTH: 40
<212> TYPE: DNA
<213> ORGANISM: Artificial Sequence
<220> FEATURE:
<223> OTHER INFORMATION: chemically-synthesized PCR primer

<400> SEQUENCE: 14
atggtaggtc tcatatcagc tatcttcatc agacggccca                        40
```